United States Patent
Hebrank et al.

(10) Patent No.: US 7,611,277 B2
(45) Date of Patent: Nov. 3, 2009

(54) METHODS AND APPARATUS FOR CANDLING AVIAN EGGS VIA THERMAL CAMERAS

(75) Inventors: John H. Hebrank, Durham, NC (US); Monika Garrell, Raleigh, NC (US)

(73) Assignee: Embrex, Inc., Durham, NC (US)

( * ) Notice: Subject to any disclaimer, the term of this patent is extended or adjusted under 35 U.S.C. 154(b) by 0 days.

(21) Appl. No.: 11/643,437

(22) Filed: Dec. 21, 2006

(65) Prior Publication Data

US 2008/0149033 A1   Jun. 26, 2008

(51) Int. Cl.
G01N 33/08 (2006.01)
G01N 25/00 (2006.01)
G01J 5/00 (2006.01)
G01K 13/00 (2006.01)
A01K 43/00 (2006.01)

(52) U.S. Cl. ............... 374/121; 374/130; 374/141; 374/4; 209/511; 356/52; 356/53

(58) Field of Classification Search .......... None
See application file for complete search history.

(56) References Cited

U.S. PATENT DOCUMENTS

| 3,060,794 A | * | 10/1962 | Reading ............... 356/57 |
|---|---|---|---|
| 4,458,630 A | | 7/1984 | Sharma et al. |
| 4,681,063 A | | 7/1987 | Hebrank |
| 4,914,672 A | | 4/1990 | Hebrank |
| 4,955,728 A | | 9/1990 | Hebrank |
| 5,017,003 A | | 5/1991 | Keromnes et al. |
| 5,028,421 A | | 7/1991 | Fredericksen et al. |
| 5,158,038 A | | 10/1992 | Sheeks et al. |
| 5,173,737 A | | 12/1992 | Mitchell et al. |
| 5,745,228 A | | 4/1998 | Hebrank et al. |
| 6,145,668 A | | 11/2000 | DePauw et al. |
| 6,149,375 A | | 11/2000 | Hebrank |
| 6,213,709 B1 | | 4/2001 | Hebrank |
| 6,224,316 B1 | | 5/2001 | Hebrank et al. |
| 6,234,320 B1 | * | 5/2001 | Hebrank ............... 209/510 |
| 6,427,844 B2 | * | 8/2002 | Hebrank ............... 209/510 |
| 6,750,954 B2 | * | 6/2004 | Hebrank et al. ........ 356/53 |
| 6,860,225 B2 | | 3/2005 | Hebrank |

* cited by examiner

*Primary Examiner*—Gail Verbitsky
*Assistant Examiner*—Mirellys Jagan
(74) *Attorney, Agent, or Firm*—Gregg C. Benson; Martha G. Munchhof

(57) ABSTRACT

Egg candling methods and apparatus are provided wherein non-live eggs, inverted egg, and side air cell eggs can be quickly identified. A method of candling eggs includes exposing a plurality of incubated eggs to an environment having a temperature different from a temperature at which the eggs were incubated; obtaining a thermal image of the eggs; and analyzing the thermal image to obtain surface temperature information for each egg. The surface temperature information is utilized to designate each egg as live/non-live, inverted, or having a side air cell.

20 Claims, 10 Drawing Sheets

METHODS AND APPARATUS FOR CANDLING AVIAN EGGS VIA THERMAL CAMERAS

FIELD OF THE INVENTION

The present invention relates generally to eggs and, more particularly, to methods and apparatus for candling eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear, rotted, and dead eggs (collectively referred to as "non-live eggs"). Non-live eggs are typically removed from incubation to increase available incubator space. In addition, removing non-live eggs can increase hatch rates by as much as 2.0% in old flocks (flock age: 58-62 weeks). This hatch improvement can have a direct value increase of about 0.2 to 0.4 ¢ per chick in the United States.

In many instances it is desirable to introduce a substance into a live egg prior to hatch. In ovo injections of various substances into avian eggs are typically employed in the commercial poultry industry to decrease post-hatch mortality rates or increase growth rates of hatched birds. Examples of substances that have been used for, or proposed for, in ovo injection include vaccines, antibiotics and vitamins. In ovo treatment substances and methods of in ovo injection are described, for example, in U.S. Pat. No. 4,458,630 to Sharma et al. and U.S. Pat. No. 5,028,421 to Fredericksen et al.

In ovo injections of substances typically occur by piercing an egg shell to create a hole therethrough (e.g., using a punch, drill, etc.), extending an injection needle through the hole and into the interior of the egg (and in some cases into the avian embryo contained therein), and injecting one or more treatment substances through the needle. An example of an in ovo injection device is disclosed in U.S. Pat. No. 4,681,063 to Hebrank. This device positions an egg and an injection needle in a fixed relationship to each other, and is designed for high-speed automated injection of a plurality of eggs. The selection of both the site and time of injection treatment can impact the effectiveness of the injected substance, as well as the mortality rate of the injected eggs or treated embryos. See, for example, U.S. Pat. No. 4,458,630 to Sharma et al., U.S. Pat. No. 4,681,063 to Hebrank, and U.S. Pat. No. 5,158,038 to Sheeks et al.

In commercial poultry production, typically only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the increasing use of automated methods for in ovo injection, and the cost of treatment substances, an automated method for accurately identifying live eggs and selectively injecting only live eggs, is desirable.

There are other applications where it is important to be able to identify live and non-live eggs. One of these applications is the cultivation and harvesting of vaccines in live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the amniotic fluid from the egg. Typically, eggs are candled before injection of a seed virus to facilitate removal of non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 5,745,228 to Hebrank et al. describes a candling apparatus that includes a photodetector and a photoemitter that are configured to be positioned on opposite sides of an egg. Light is generated in short bursts from each photoemitter and the corresponding photodetector monitors while it's corresponding photoemitter is operational. A flat of eggs is continuously "scanned" as it moves through the candling apparatus with each detector-source pair active while at least adjacent, and preferably all other, pairs are quiescent.

Thermal-based candling systems can detect rotted eggs in egg streams of up to between about 50,000-100,000 eggs per hour. Unfortunately, because of egg-to-egg thermal variations, thermal-based candling systems may misidentify live and non-live eggs. In addition, thermal-based candling systems may be less accurate with embryos that generate less heat than day 17 eggs.

Embryo heartbeat (pulse) detection methods are known that can detect live eggs with a high degree of accuracy. For example, U.S. Pat. No. 6,860,225 to Hebrank describes candling methods and apparatus wherein cyclical variation in light intensity indicates the existence of an embryo pulse. U.S. Pat. No. 5,173,737 to Mitchell describes a method of determining whether an egg contains a live embryo by directing light into an egg to stimulate embryo movement, and then measuring resulting embryo movement. Unfortunately, the Mitchell method may be time-consuming and may not accurately detect live embryos that do not move as a result of light stimulation.

Conventionally, it is desirable for eggs to be placed within a carrier for incubation and in ovo processing with the narrow end down such that the air cell therewithin is facing upwardly. Unfortunately, because some eggs are nearly spherical in shape, it can be difficult to determine which end is the narrow end of an egg. Inverted eggs (i.e., eggs oriented within a carrier such that the air cell is on the bottom or side) are about 30% less likely to hatch than eggs oriented with the air cell upwardly. In addition, in ovo injection of inverted eggs may pierce the embryo and yolk rather than just the amnion, and may damage one or more membranes. If inverted eggs are utilized in vaccine production, seed vaccine may not be placed in the correct egg compartment and material may spill therefrom during harvesting operations, which is undesirable. Similarly, eggs with side air cells are considered undesirable for vaccine production since these also tend to spill contents during harvesting.

Unfortunately, existing candling techniques may not be capable of detecting inverted eggs. As such, a need exists for a candling technique that can rapidly detect live and non-live eggs and that can also detect inverted eggs within a carrier.

SUMMARY OF THE INVENTION

In view of the above discussion, egg candling methods and apparatus are provided wherein non-live eggs, inverted egg, and side air cell eggs can be quickly identified. According to some embodiments of the present invention, a method of candling eggs includes exposing a plurality of incubated eggs to an environment having a temperature different from a temperature at which the eggs were incubated; obtaining a thermal image of the eggs; and analyzing the thermal image to obtain surface temperature information for each egg. According to some embodiments of the present invention, obtaining a thermal image of the eggs includes obtaining a thermal image of downwardly facing surfaces of the eggs in a carrier, and designating an egg as non-live if the surface temperature of a central region of the downwardly facing surface of the egg compared to the surface temperatures of central regions of the downwardly facing surfaces of adjacent eggs is lower by a predetermined amount.

According to some embodiments of the present invention, obtaining a thermal image of the eggs includes obtaining a thermal image of downwardly or upwardly facing surfaces of the eggs in a carrier, and designating an egg as an inverted egg if the surface temperature of the egg compared to the surface temperature of corresponding downwardly or upwardly facing surfaces of adjacent eggs is lower or higher by a predetermined amount.

According to some embodiments of the present invention, obtaining a thermal image of the eggs includes obtaining a thermal image of downwardly facing surfaces of the eggs in a carrier, and designating an egg as an inverted egg if the downwardly facing surface has two regions with respective different temperatures, and wherein the temperature difference is greater than a predetermined amount.

According to some embodiments of the present invention, the difference between the upward facing surface temperature of each egg in a carrier with the average surface temperature of adjacent eggs is calculated. An egg is designated as inverted if a surface temperature of the egg exceeds this average surface temperature of adjacent eggs by a predetermined amount.

According to some embodiments of the present invention, obtaining a thermal image of the eggs includes obtaining top and bottom thermal images of the upwardly facing and downwardly facing egg surfaces, respectively. The respective top and bottom thermal images for each egg are then compared to determine which surface of each egg has the higher temperature. An egg is designated as inverted if the temperature of the upwardly facing surface is higher than the temperature of the respective downwardly facing surface.

According to some embodiments of the present invention, obtaining a thermal image of the eggs includes obtaining a thermal image of upwardly facing surfaces of the eggs in the carrier, and designating an egg as an inverted egg if the temperature of the upwardly facing surface of the egg is uniform thereacross.

According to some embodiments of the present invention, obtaining a thermal image of the eggs includes obtaining a thermal image of downwardly or upwardly facing surfaces of the eggs in the carrier, and further comprising designating an egg as having an air cell located on a side portion of the egg if the temperature of an edge portion of the egg surface is lower than a temperature of the remaining portion of the egg surface.

According to some embodiments of the present invention, eggs are removed from a carrier and rotated as a thermal image is being obtained.

According to some embodiments of the present invention, an apparatus for candling eggs includes a thermal imaging camera configured to obtain a thermal image of a plurality of eggs supported in a carrier, and a processor in communication with the thermal imaging camera that is configured to analyze a thermal image of the eggs, obtain surface temperature information for each egg, and designate each egg as live/non-live, inverted, or having a side air cell.

DETAILED DESCRIPTION OF EMBODIMENTS OF THE INVENTION

Figure 1:
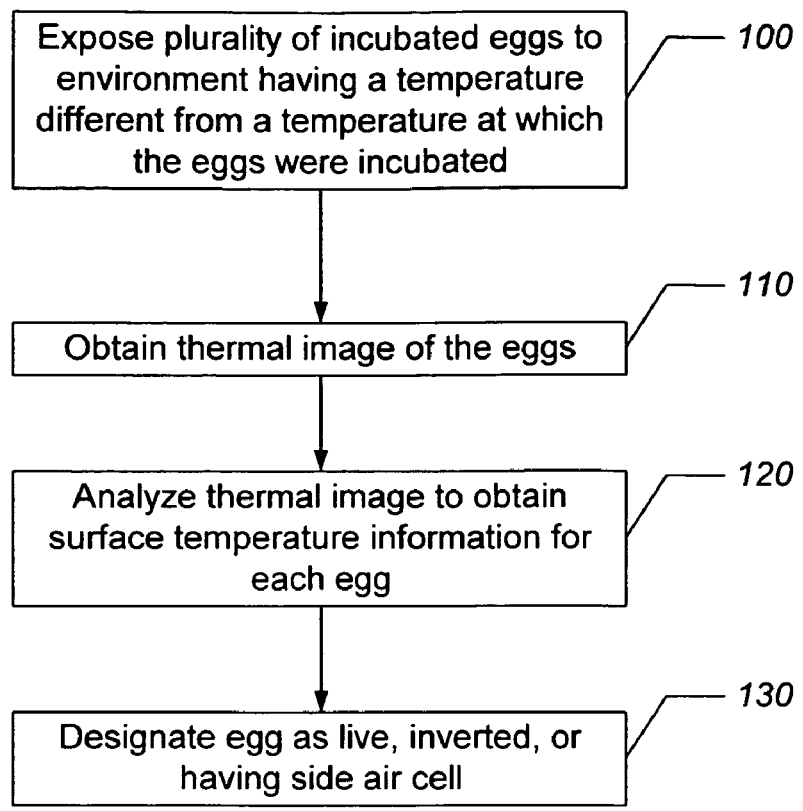
FIG. 1 is a flow chart of operations for detecting live/non-live eggs, inverted eggs, and side air cell eggs, according to some embodiments of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. All publications, patent applications, patents, and other references mentioned herein are incorporated herein by reference in their entireties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

The term "inverted egg" as used herein means an egg placed within a carrier such that the air cell therewithin is located on the bottom of the egg and not at the upwardly facing end of the egg.

The term "side air cell egg" as used herein means an egg placed within a carrier such that the air cell therewithin is located on a side portion of the egg and not completely at the upwardly or downwardly facing ends of the egg.

According to some embodiments of the present invention, non-live eggs can be detected by analyzing thermal images of the eggs. In addition, the location of air cells within eggs can be detected by analyzing thermal images of the eggs. As known to those skilled in the art of the present invention, in any given environment, the shell temperature over most of an egg will approach the temperature of the contents of the egg. For example, the contents of a Day 17 to 18 egg are about one degree Celsius (° C.) higher than the temperature of the environment surrounding the egg during incubation. When eggs are removed from an incubator, an egg and its contents cool slowly to room temperature over a period of about one to two hours. The temperature of an air cell is roughly half way between room temperature and the temperature of the egg contents. The temperature of the shell over an air cell drops to a temperature closer to the surrounding environment in less than a minute after an egg is removed from an incubator.

A thermal camera (i.e., an infrared camera) according to some embodiments of the present invention can detect the air cell in an egg because of the relatively large temperature differential between the air cell and surrounding portions of the egg. An air cell facing upwardly will appear in a thermal image as a cool generally circular area having a diameter of, for example, about two-thirds the diameter of the egg. Inverted eggs wherein the air cell is located on the bottom of the egg will appear in a thermal image with little or no upwardly facing cool area. Eggs with an air cell located on the side thereof will appear in a thermal image with a small cool area along a side portion of the egg.

Referring initially to FIG. 1, methods of detecting live eggs, inverted eggs, and side air cell eggs, according to some embodiments of the present invention, are illustrated. A plurality of presumably live eggs are removed from an incubator and placed into an environment having a temperature different from a temperature at which the eggs were incubated (Block 100). This environment may have a temperature that is higher than the incubation temperature or a temperature that is lower than the incubation temperature.

As would be understood by one skilled in the art, eggs are incubated and processed within a carrier, such as an egg flat. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein. The terms "flat" and "carrier" are intended to be used interchangeably herein.

Figure 2:
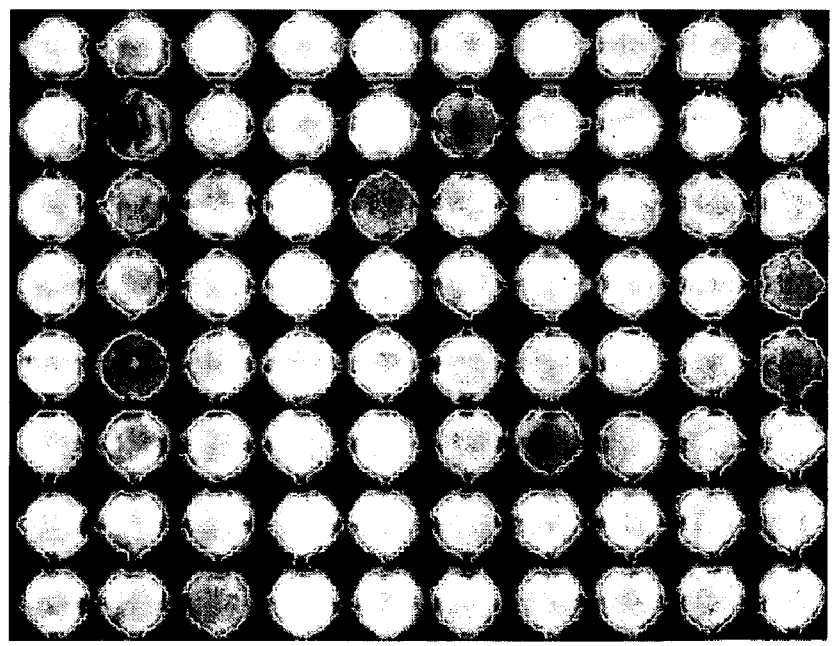
FIG. 2 illustrates a thermal image of a flat of eggs taken from above the eggs via a thermal camera, according to some embodiments of the present invention.

After being removed from an incubator, a thermal image of the eggs within the carrier is obtained via a thermal camera (i.e., camera configured to capture infrared wavelength images) (Block 110). An exemplary thermal image of a plurality of eggs in a carrier is illustrated in FIG. 2. Exemplary thermal cameras that may be utilized in accordance with embodiments of the present invention include, but are not limited to, the FLIR ThermoVision® A20 and the FLIR ThermoVision® 320 cameras, available from FLIR Systems, Inc., Wilsonville, Oreg. Obtaining a thermal image may include obtaining an image of the upwardly facing surfaces of the eggs, obtaining an image of the downwardly facing surfaces of the eggs, or obtaining an image of both the upwardly and downwardly facing surfaces of the eggs. According to some embodiments of the present invention, an egg carrier may be placed within an enclosure that shrouds the eggs and thermal camera from infrared emissions from external sources.

The thermal image of the eggs is digitized and then analyzed to obtain surface temperature information for each egg (Block 120). Using the surface temperature information, each egg is then designated as live/non-live, inverted, or as having an air cell located in the side of the egg (i.e., a side air cell egg) via an identification algorithm (Block 130).

Thermal images of eggs can be obstructed by feathers and debris, including debris from exploded rotten eggs (referred to as "poppers"). Commercially available image analysis programs, such as Mathworks' Matlab Image Toolbox, for example, offer various digital image processing and algorithm development tools, such as histogram equalization and stretching, morphological opening or closing of images, image dilation and erosion, edge finders, and maxima/minima transforms that can be utilized to minimize the effects of feathers and debris. For example, image dilation and erosion coupled with maxima and minima transforms can be used to focus on high intensity areas by allowing warm areas of individual eggs to be isolated. Since high intensities correspond directly to higher temperatures, Applicants have found that egg temperatures can be measured without influence from extraneous material and debris. Image dilation adds pixels to the boundaries of an object in an image in a predefined fashion, increasing the effective object area, while image erosion removes pixels from the boundaries of the object so that all objects smaller than a predefined area are eroded from the image. The amount of pixels added or removed is controlled by predefined elements.

Histogram equalization and histogram stretching may be utilized to overcome problems presented by non-constant thermal environments in which thermal images are obtained. For example, a technique called "contrast-limited adaptive histogram equalization" that operates on small areas in an image, referred to as "tiles", can be used. Tiles are rectangular areas of a thermal image and can be described as defined zones of interest. The size of a tile corresponds to the size of a cradle in which each individual egg sits in a flat. An equalization procedure can enhance the contrast in each tile, so that the histogram of each output region approximates a predefined histogram. These tiles can then be recombined using, for example, bilinear interpolation to eliminate artificially induced boundaries.

Once various imaging techniques have been applied to a thermal image of eggs to reduce the effects of feathers and debris and to overcome the effects of non-constant thermal environments, the thermal image can be analyzed as described below to determine which eggs are live/non-live, inverted, or side air cell eggs.

Identification Algorithm

Figure 3A:
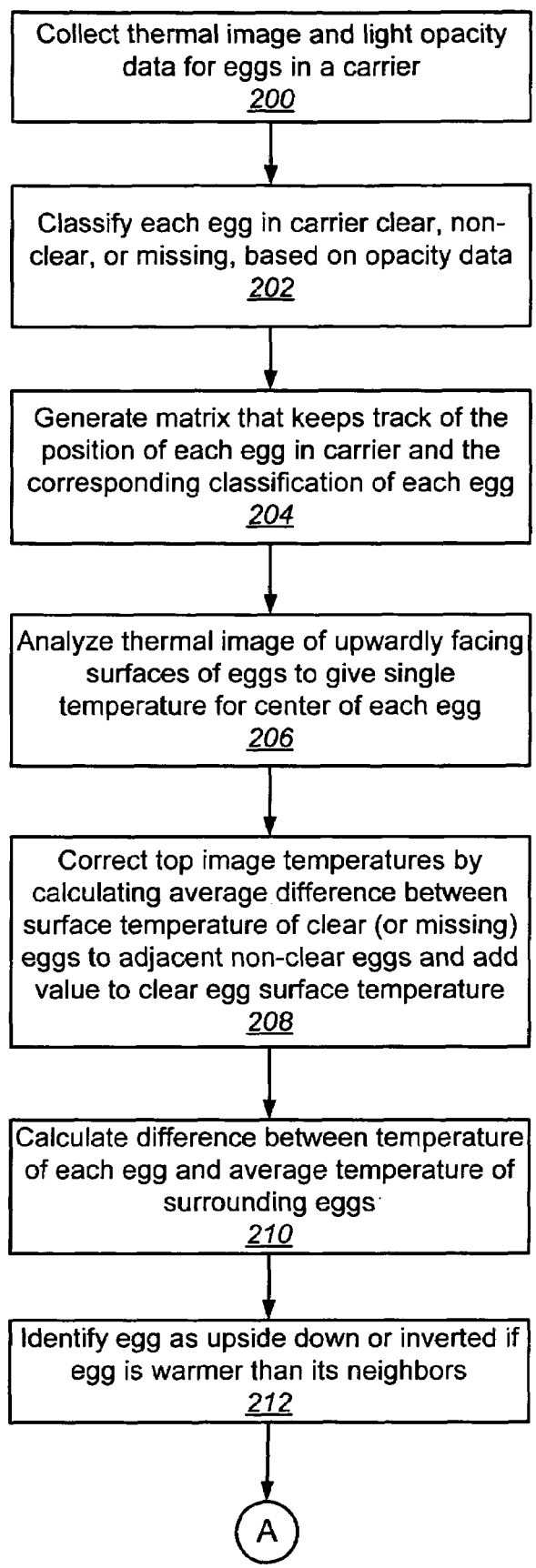
FIGS. 3A-3C are flow charts illustrating operations of an identification algorithm that is configured to designate eggs as live/non-live or inverted, according to some embodiments of the present invention.
Figure 3B:
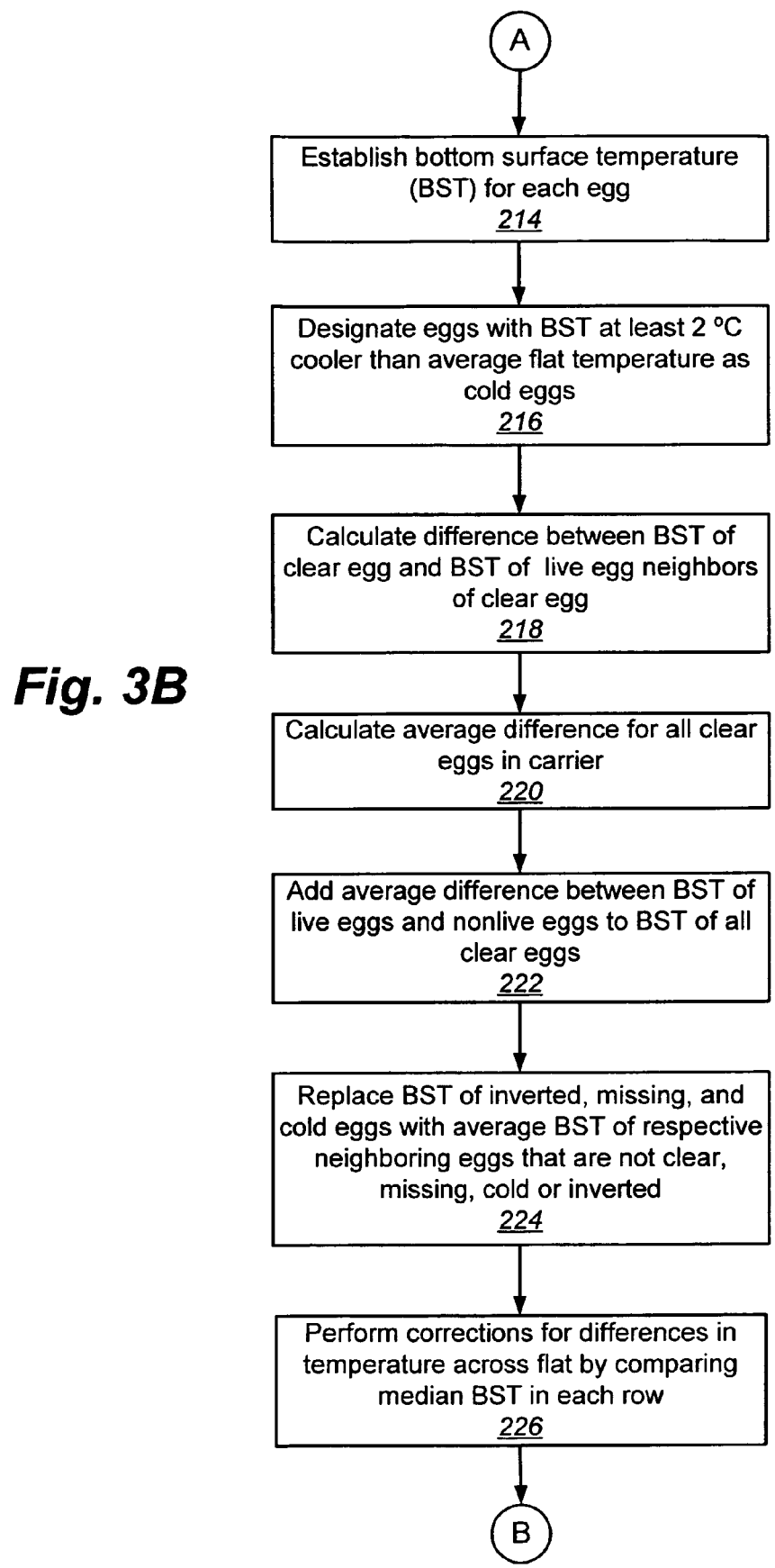
Figure 3C:
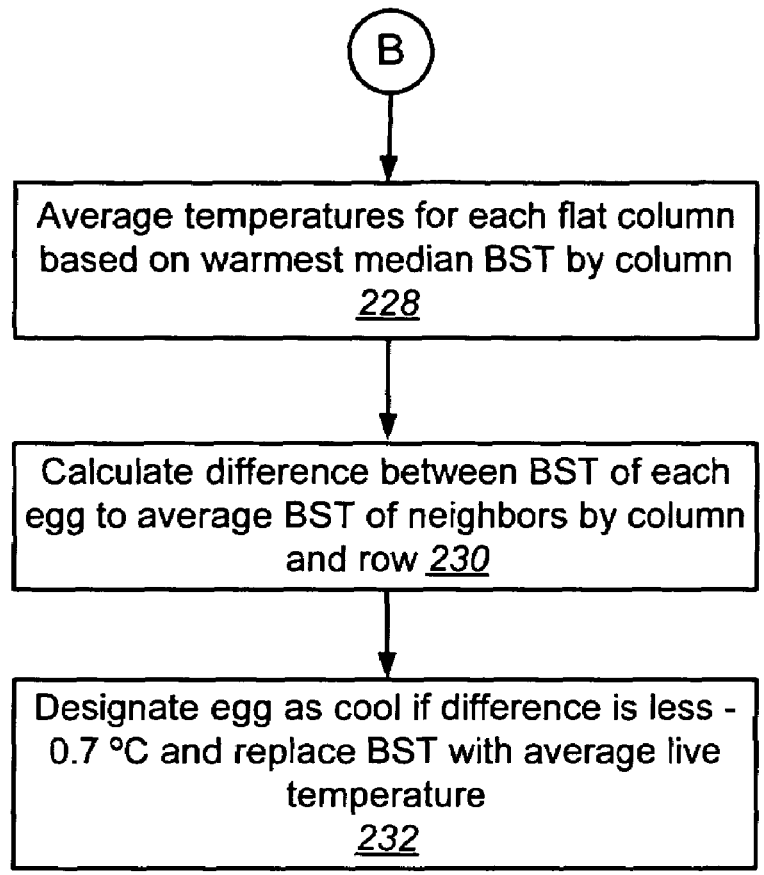

Referring to FIGS. 3A-3C, a sequence of operations for designating each egg as live/non-live or inverted, according to some embodiments of the present invention, is illustrated. Thermal image and light opacity data for eggs in a carrier are initially collected (Block 200) and each egg in the carrier is designated as clear, non-clear, or missing, based on the opacity data (Block 202). All other eggs in the carrier are designated as live and this designation can be modified as information is obtained in further processing. A matrix is generated that keeps track of the position of each egg in the carrier and the corresponding designation of each egg (i.e., live, clear, missing, cool, cold) (Block 204).

The thermal image of the upwardly facing surfaces of the eggs in the carrier (referred to as the "top image") captured by the thermal camera is then analyzed to give a single temperature for the center of each egg (Block 206). Then top image temperatures are corrected by calculating the average difference between the surface temperature of designated clear eggs to adjacent non-clear eggs and the value is added to the clear egg surface temperature (Block 208). The difference between the temperatures of each egg to the average temperature of the surrounding eggs is calculated (Block 210). If the difference is greater than 1.0° C. (i.e., the egg is warmer than its neighbors), the egg is designated as upside down or inverted in the egg condition matrix, i.e., the egg is identified as an upside down or inverted egg in the egg condition matrix (Block 212).

Using the image of the downwardly facing surfaces of the eggs in the carrier (referred to as the "bottom image") captured by the thermal camera, image processing thereof establishes a bottom surface temperature (BST) for each egg (Block 214). Eggs having a very cold BST (e.g., eggs with a BST at least 2° C. cooler than average flat temperature) are designated as cold (Block 216). The difference between the BST of eggs designated as clear eggs and the BST of each clear egg's live neighbors (i.e., eggs adjacent to a specific clear egg that are designated as live in the egg condition matrix) is calculated (Block 218) and an average difference is calculated for all clear eggs in the carrier (Block 220). The average calculation excludes eggs designated as cold, inverted or missing. The average live/nonlive difference is added to the BST of all clear eggs (Block 222). The BST of inverted, missing, and cold eggs is replaced with this average BST of their respective neighbor eggs that are not clear, missing, cold or inverted (Block 224).

Corrections are then performed for the differences in egg temperatures across a carrier by comparing the median BST in each row (Block 226). This correction is performed by averaging the median BST eggs for all the rows and then comparing the median BST for each row to the overall average. The BST temperatures for all the eggs in each row is then boosted by the amount the row's median BST egg is below the overall average. This operation is performed for all the rows. Corrections are then performed for the columns of egg in each carrier (Block 228). Column correction is done by first averaging the median BST eggs for each column and then comparing the median BST for each column to the overall average. The BST temperatures for all the eggs in each column is then boosted by the amount the column's median BST egg is below the overall average. This operation is performed for all the columns. The difference between BST of each egg to the average BST of their neighbors are calculated (Block 230). If the differences are less −0.7° C., the eggs are designated as cool in the egg condition matrix and its BST is replaced with the average live temperature (Block 232). The steps of Blocks 230-232 are repeated until no additional cool eggs are found.

Non-Live Egg Designation

According to some embodiments of the present invention, an egg is designated as non-live if the surface temperature of a central region of the downwardly facing surface of the egg compared to the surface temperatures of central regions of the downwardly facing surfaces of adjacent eggs is lower by a predetermined amount. The term "adjacent eggs" refers to the eggs directly neighboring a particular egg in a carrier. Applicants have found that an egg with a temperature at a central region of the downwardly facing surface that is generally between 0.5° C. and 2.5° C. cooler than that of neighboring eggs will be a non-live egg. In particular, Applicants have found that an egg that is more than 2° C. colder than the eggs adjacent to it is either a non-live or inverted egg. In addition, Applicants have found that, after corrections for temperature differences across the flat, an egg that is more than 1° C. cooler than the average temperature of live eggs surrounding the egg is non-live, also.

Because the temperature of eggs in a carrier can be non-uniform (e.g., outside rows and columns cool down at a higher rate, while eggs on the interior of a flat are less exposed to cooler outside air and may keep each other warm), identification algorithms, according to embodiments of the present invention, take into consideration where an egg is located in a carrier when analyzing the surface temperature information. In addition, because multiple carriers are typically incubated at the same time and typically are arranged in a stack, the position of a carrier in a stack is also taken into consideration by identification algorithms. According to some embodiments of the present invention, the identification algorithm utilizes an averaging procedure that compares median temperatures of eggs in rows and columns and adjusts all eggs in a row or column based on the temperature of the median egg in each row or column. Median temperatures are used because they tend to be more statistically stable than average temperatures by avoiding variation from averaging in very high or very low temperatures.

Inverted Egg Designation

Figure 4A:
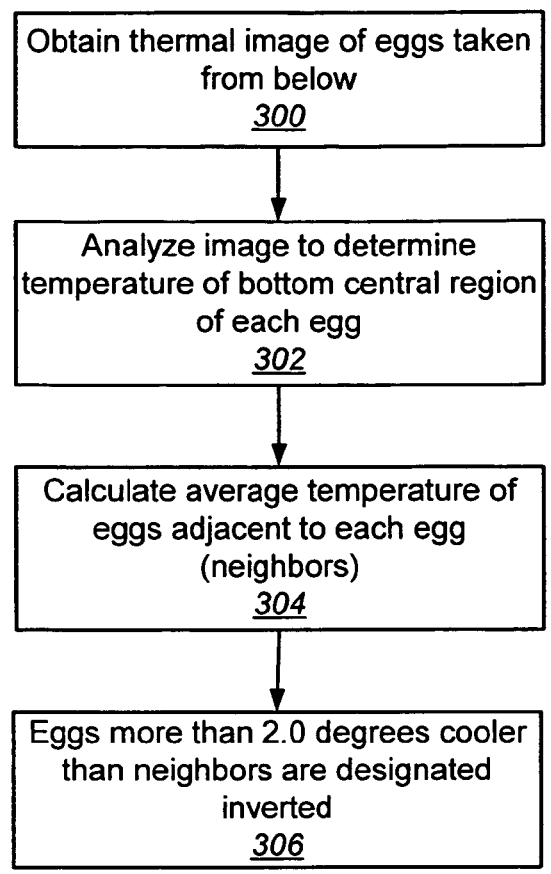
FIGS. 4A-4C are flow charts that illustrate operations for identifying inverted eggs, according to some embodiments of the present invention.

According to some embodiments of the present invention, an egg may be designated as an inverted egg if the temperature of the downwardly facing surface of the egg compared to the temperatures of downwardly facing surfaces of adjacent eggs is lower by a predetermined amount. Because the air cell of an egg acts as thermal insulation, the air cell end of an egg will be cooler than other portions of the egg. As such, if the downwardly facing surface of an egg is cooler than the downwardly facing surfaces of adjacent eggs in a carrier, it is likely that the egg is upside down (i.e., inverted) in the carrier. For example, referring to FIG. 4A, a thermal image of a flat of eggs is taken from below (Block 300). The image is analyzed to determine the temperature of the bottom central region of each egg (Block 302). The average temperature of eggs adjacent to each egg is calculated (Block 304), and eggs that are more than 2.0 degrees cooler than their neighbors are designated as inverted (Block 306).

Figure 4B:
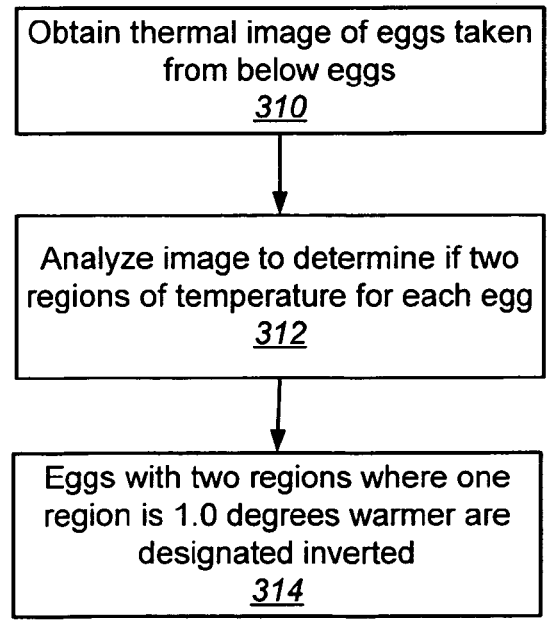
Figure 5:
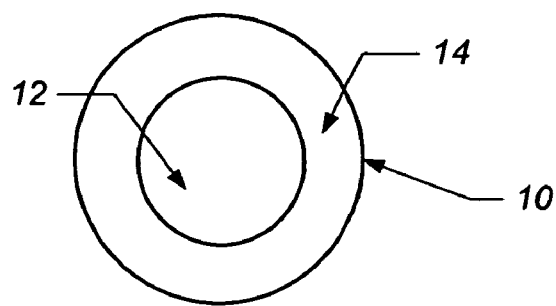
FIG. 5 illustrates the appearance of a thermal image of an end of an egg having an air cell located at the end.

In addition, an egg may be designated as an inverted egg if the downwardly facing surface of the egg has two regions with respective different temperatures, and if the temperature difference is greater than a predetermined amount. As illustrated in FIG. 5, a thermal image of an end of an egg 10 having an air cell will appear as two regions: a central region 12 and a peripheral region 14 that circumscribes the central region 12. The surface temperature of the central region 12 will be lower than the surface temperature of the peripheral region 14. In addition, the two regions (12, 14 in FIG. 5) typically will each comprise at least 10% of the total surface area of the egg in the thermal image. For example, referring to FIG. 4B, a thermal image of a flat of eggs is taken from below (Block 310). The image is analyzed to determine if there are two temperature regions for each egg (Block 312). Eggs with two temperature regions where one region is 1.0 degree warmer are designated as inverted (Block 314).

Figure 4C:
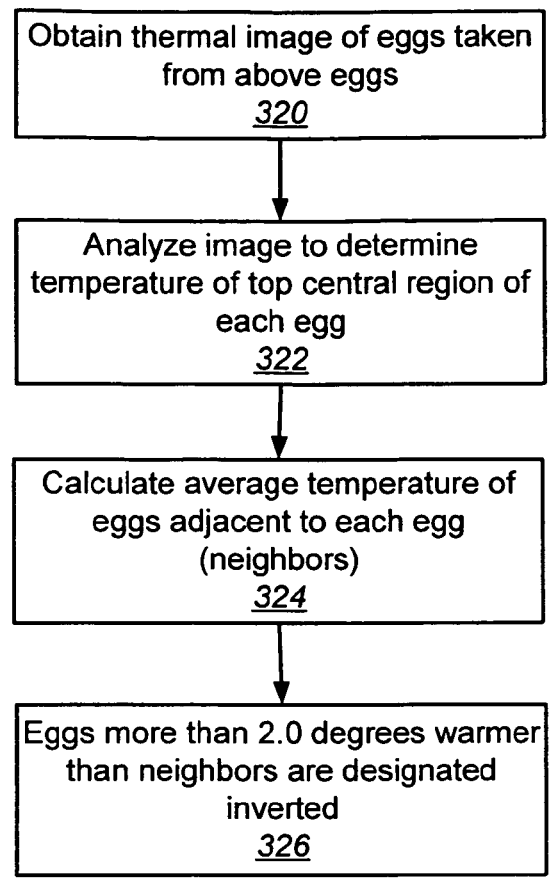

In addition, an egg may be designated as an inverted egg if the surface temperature of the upwardly facing surface of the egg is higher than the upwardly facing surface temperatures of adjacent eggs. As discussed with respect to FIG. 5, the air cell in an egg will act as an insulator and the surface temperature at the end of an egg where the air cell is located will be cooler than other portions of the egg. Thus, if an egg is inverted, the air cell will not be present at the upwardly facing end and the surface temperature of the upwardly facing end will be higher than that of adjacent eggs that have air cells at the upwardly facing ends thereof. For example, referring to FIG. 4C, a thermal image of a flat of eggs is taken from above (Block 320). The image is analyzed to determine the temperature of the top central region of each egg (Block 322). The average temperature of eggs adjacent to each egg is calculated (Block 324), and eggs that are more than 2.0 degrees warmer than their neighbors are designated as inverted (Block 326).

According to some embodiments of the present invention, an egg may be designated as an inverted egg if the temperature of the upwardly facing surface of the egg exceeds the average surface temperature of adjacent eggs by a predetermined amount.

According to some embodiments of the present invention, an egg may be designated as an inverted egg if a thermal image is obtained of both the upwardly facing and downwardly facing surfaces of an egg and if the temperature of the upwardly facing surface is higher than the temperature of the downwardly facing surface.

According to some embodiments of the present invention, an egg may be designated as an inverted egg if a temperature of the upwardly facing surface of an egg is uniform thereacross. As discussed above, the thermal image of an end of an egg having an air cell will appear as illustrated in FIG. 5 and will not have a uniform temperature thereacross because of the presence of the air cell. Thus, conversely, the surface temperature of an end of an egg not having an air cell will be substantially uniform thereacross.

Side Air Cell Egg Designation

Figure 4D:
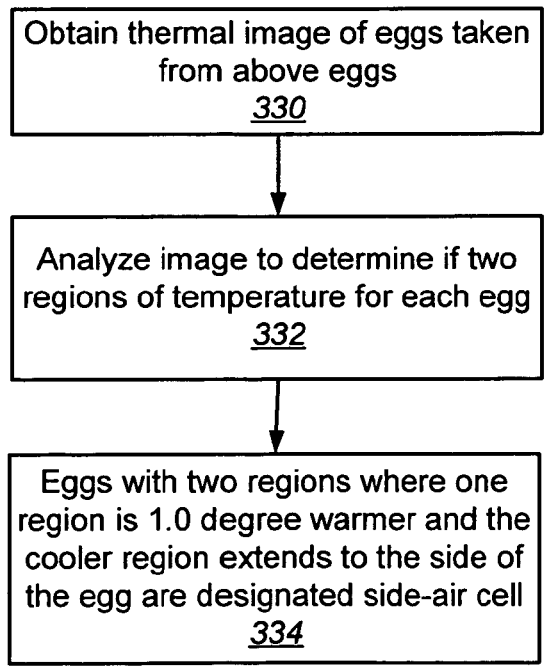
FIGS. 4D-4E are flow charts that illustrate operations for identifying side air cell eggs, according to some embodiments of the present invention.
Figure 6:
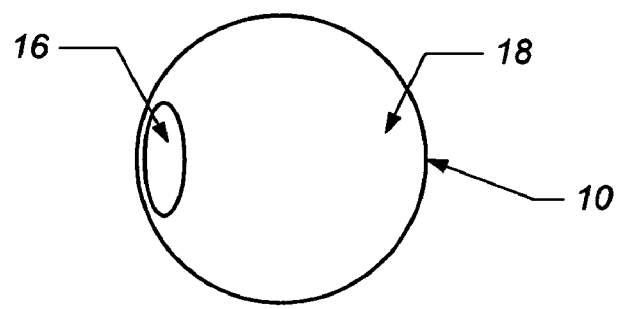
FIG. 6 illustrates the appearance of a thermal image of an end of an egg having an air cell located in a side portion of the egg.

According to some embodiments of the present invention, an egg may be designated as a side air cell egg if the temperature at an edge portion of the egg surface is lower than a temperature of the remaining portion of the egg surface. As illustrated in FIG. 6, a thermal image of an end of an egg 10 having an air cell located not at the end but at a side portion of the egg will appear as two regions: a cooler region 16 at a side portion/region and a remaining region 18 that has a higher temperature. This applies to a thermal image of either the upwardly facing surface of an egg or the downwardly facing surface of the egg. The term "side portion" is intended to include any edge and/or side region visible in the thermal image of the top or bottom of an egg. For example, referring to FIG. 4D, a thermal image of a flat of eggs is taken from above (Block 330). The image is analyzed to determine if two temperature regions exist for each egg (Block 332). Eggs with two temperature regions where one region is 1.0 degree warmer and wherein the cooler region extends to the side of the egg are designated as side air cell eggs (Block 334).

Figure 4E:
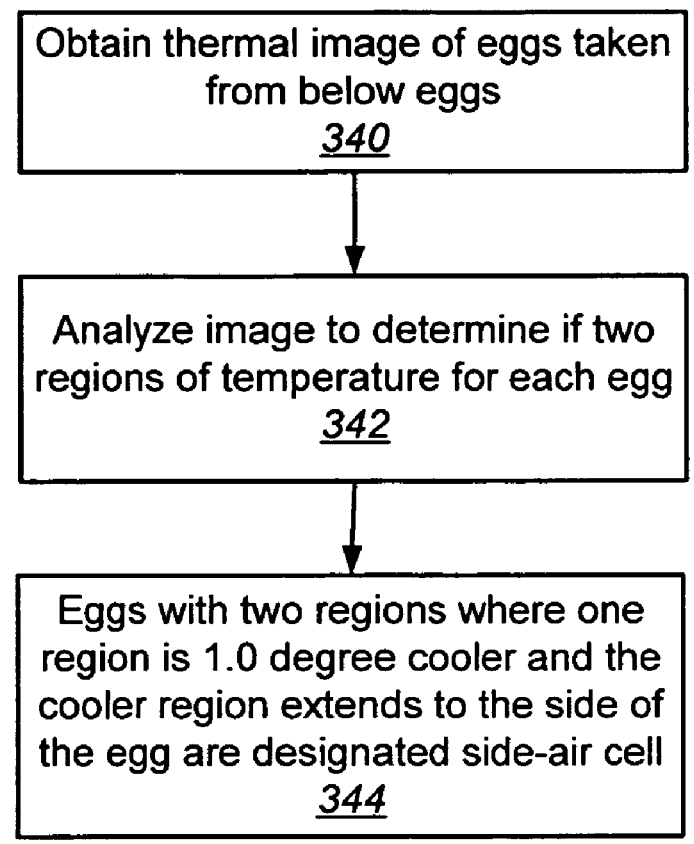

Referring to FIG. 4E, a thermal image of a flat of eggs is taken from below (Block 340). The image is analyzed to determine if two temperature regions exist for each egg (Block 342). Eggs with two temperature regions where one region is 1.0 degree cooler and wherein the cooler region extends to the side of the egg are designated as side air cell eggs (Block 344).

Figure 7:
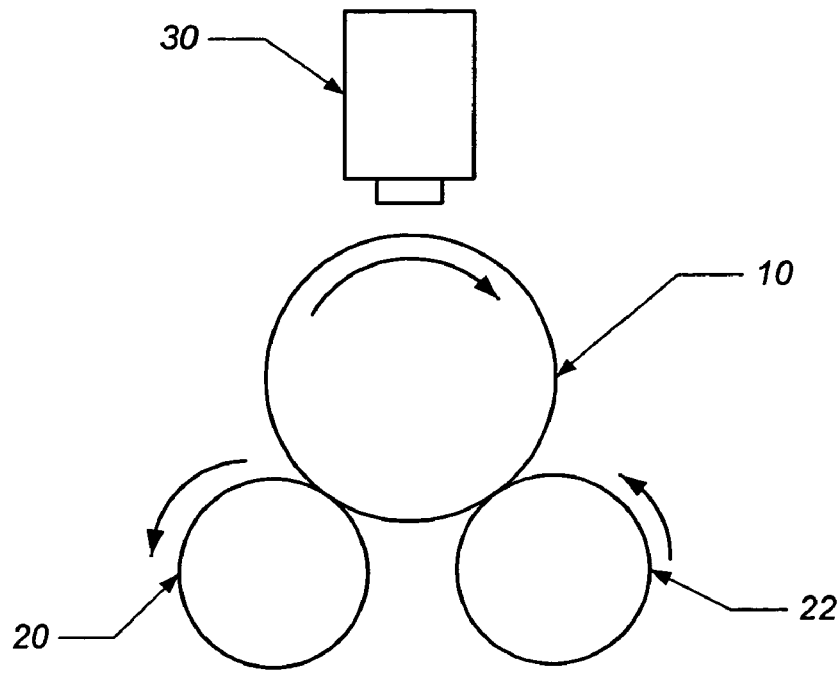
FIG. 7 illustrates an egg being rotated by a pair of spaced-apart rollers as a thermal camera obtains a thermal image of the egg, according to some embodiments of the present invention.

Referring to FIG. 7, eggs may be removed from a carrier and placed in a device that rotates the eggs as a thermal image of the eggs is being obtained, according to some embodiments of the present invention. For example, in the illustrated embodiment, an egg 10 is placed between two rollers 20, 22 that rotate in the same direction. The rotating rollers 20, 22 cause the egg 10 to rotate about its axis. A thermal camera 30 is positioned above the rotating egg 10 and captures a thermal image of the entire surface of the egg 10 as it rotates about its axis.

Egg Processing System

Figure 8:
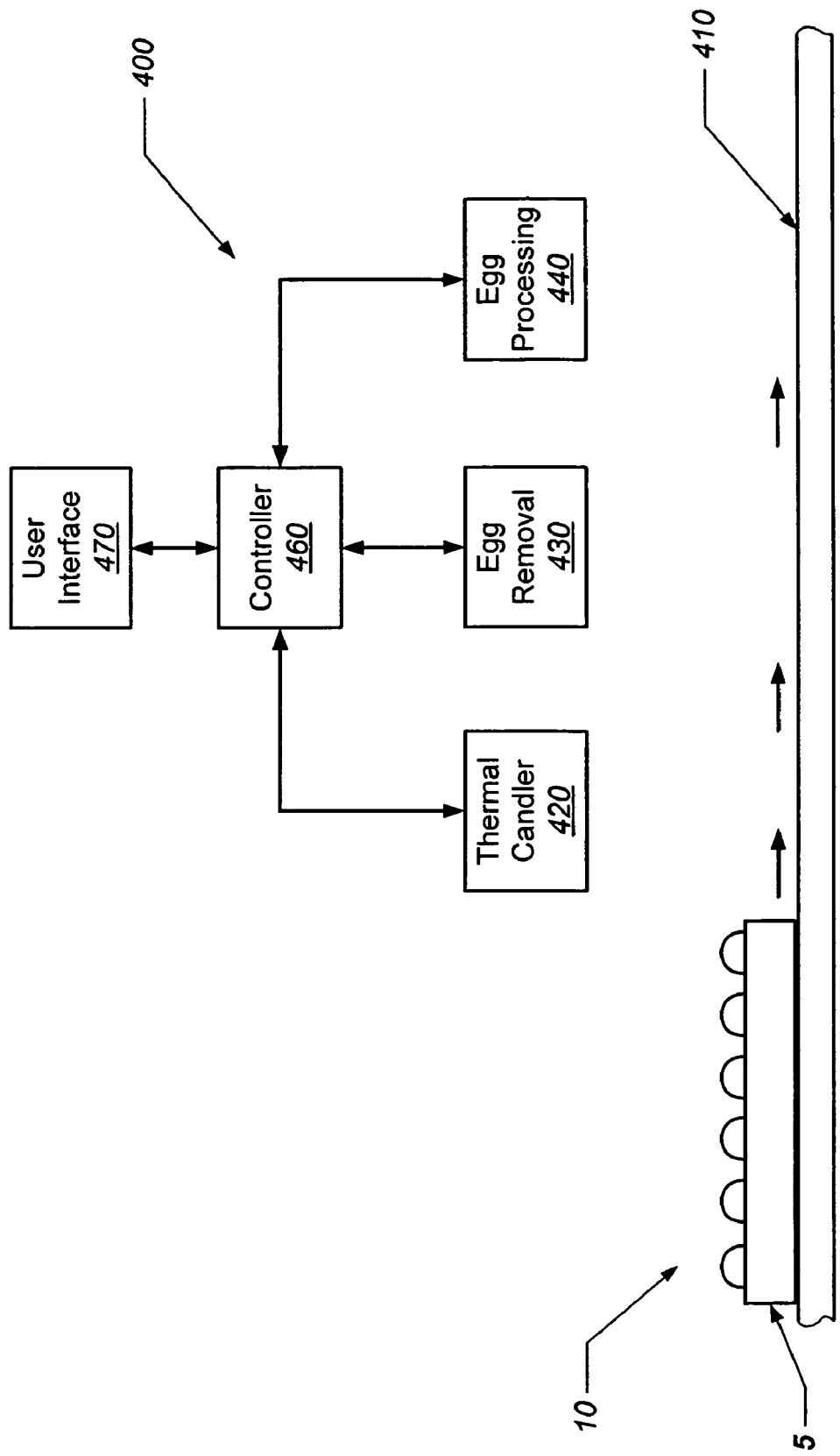
FIG. 8 is a block diagram of an egg processing system, according to some embodiments of the present invention.
Figure 9:
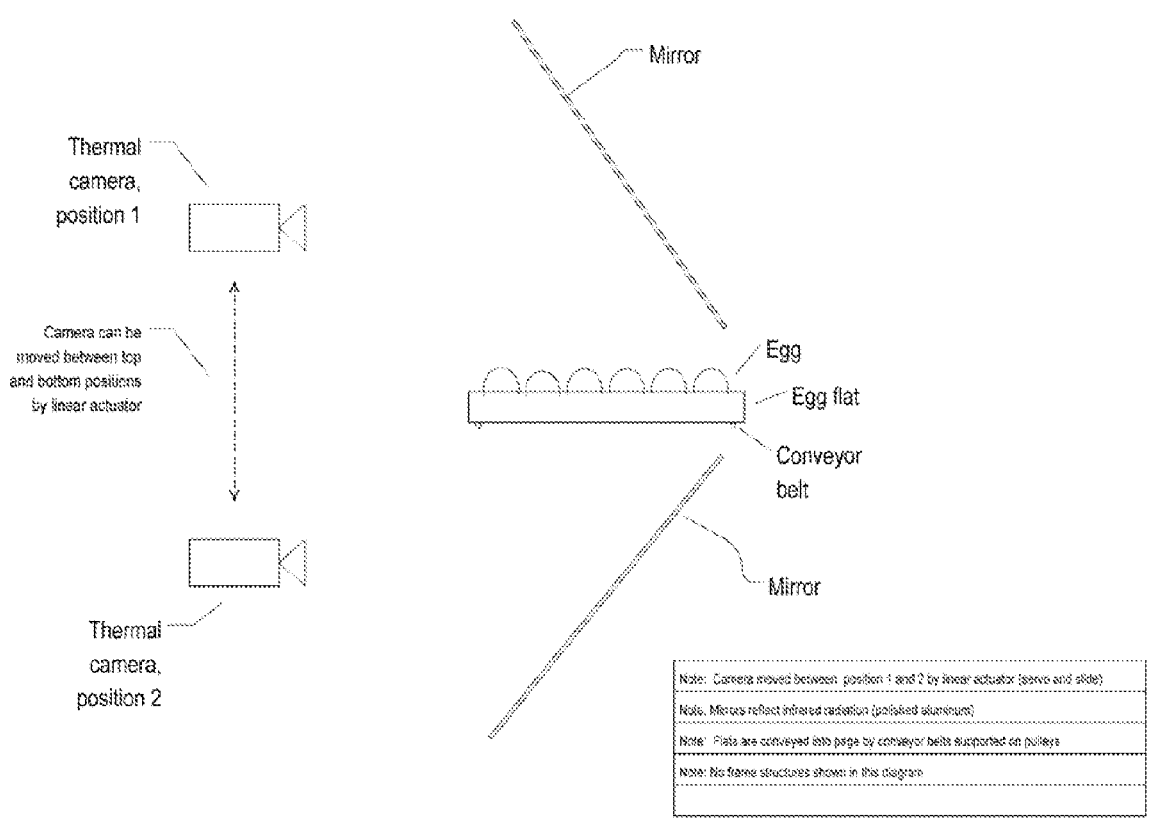
FIG. 9 illustrates the configuration of mirrors such that a camera is able to obtain a thermal image of both ends of the egg, either at the same time or sequentially.

Referring to FIG. 8, a block diagram of an egg processing system 400, according to some embodiments of the present invention, is illustrated. The illustrated system 400 includes a conveyor system 410 that conveys flats (or other carriers) 5 of eggs 10, and a thermal candling station 420, operably associated with the conveyor system 410 and with a controller 460, that identifies live/non-live eggs, inverted eggs and side air cell eggs as described above. The illustrated system 400 also includes an egg removal station 430 that is configured to selectively remove eggs (e.g., live or non-live eggs; inverted eggs, side air cell eggs) from an egg flat 5, and an egg processing station 440.

In operation, a flat 5 of eggs 10 is conveyed from an incubator to the thermal candling station 420 via the conveyor system 410. Various types of conveyor systems may be utilized with embodiments of the present invention. Egg conveying systems are well known to those of skill in the art and need not be described further herein. The thermal candling station 420 includes one or more thermal cameras (e.g., a FLIR ThermoVision® A20, FLIR ThermoVision® 320 camera, etc.) that is configured to capture a thermal image of some or all of the eggs 10 in the flat 5. According to some embodiments of the present invention, a thermal camera may be configured to obtain a thermal image of the upwardly facing surfaces of the eggs 10 and another thermal camera may be configured to obtain a thermal image of the downwardly facing surfaces of the eggs 10. These thermal cameras can be position adjacent the respective ends of the eggs 10, for example. According to some embodiments of the present invention, a single thermal camera can be utilized with one or more mirrors to let the camera see both ends of an egg, either at the same time or sequentially.

A controller 460 controls operations of the thermal candling station 420, the conveyor system 410, the egg removal station 430, and the egg processing station 440. The controller 460 is configured to accurately and quickly position the thermal camera of the thermal candling station 420 relative to a flat of eggs 10. The controller 460 is configured to store and analyze thermal images of eggs captured by the thermal candling station 420 as described above with respect to FIGS. 3A-3C and FIGS. 4A-4E. Alternatively, the controller 460 may transmit captured thermal images to an external processor for analysis. An operator interface (e.g., a display) 470 may be provided to allow an operator to interact with the controller 460.

Eggs designated as non-live, inverted, or side air cell eggs may be removed from the flat 5 via egg removal station 430. Alternatively, inverted eggs may be reoriented within the carrier with the air cell end facing upwardly. The egg removal station 430 may be a manual station wherein the designated non-live eggs are removed by hand. Alternatively, the egg removal station 430 may operate automatically and robotically. For example, the egg removal station 430 may employ suction-type lifting devices as disclosed in U.S. Pat. No. 4,681,063 or in U.S. Pat. No. 5,017,003. Various devices and methods for automatically and robotically removing eggs from a flat and transporting same to another location may be utilized with embodiments of the present invention without limitation. Exemplary egg removal apparatus that may serve the function of the egg removal station 430 are described in U.S. Pat. Nos. 6,145,668; 6,149,375; 6,213,709; and 6,224,316.

Flat 5 at this point on the conveyor 410 contains only non-inverted live eggs and can proceed to processing station 440 (e.g., inoculation, vaccine production, material sampling, etc.). An exemplary processing station 440 is the INOVOJECT® automated injection system (Embrex, Inc., Research Triangle Park, N.C.). However, various other processing stations capable of in ovo delivery and/or removal may be used in accordance with some embodiments of the present invention.

Experimental Results

Day 18 Results

On three different days, a total of 28,800 Day 18 eggs from both a prime and an old flock (33 and 51 weeks) were processed and analyzed. Phase II ended after achieving 99.93% correctly identified lives, 99.91% correctly identified non-lives, and 99.95% correctly identified upside down eggs, flock age proved not to influence accuracy of live/dead determination. (A complete table of our test data can be found in the Appendix).

Day 16 Results

Additionally, we imaged and analyzed 9,600 of Day 16 eggs (Day 15.5) from a prime flock (33 weeks). Older flock eggs were excluded from this study since Day 18 analysis showed no difference in accuracy for the analysis of prime and older flock eggs. After breakout, it was established that 99.98% of lives were correctly identified and 99.32% of non-lives were correctly detected, as well as 100% of upside down placed eggs.

It was found that the factor contributing most to the high error stemmed from eggs being identified as "late middle dead" during necropsy. "Late middle dead" as used in our classification describes an embryo that died between Day 15 and Day 18. Since it can reasonably be assumed that these "late middle dead" embryos were indeed still live on Day 15.5, the corrected statistic reads as follows: 99.98% correctly identified lives, 99.90% correctly identified non-lives, and 100% correctly identified upside downs.

| Correctly identified | Day 18 | Day 15½ | Day 15½ without LM* |
|---|---|---|---|
| Lives | 99.93% | 99.98% | 99.98% |
| Non-Lives | 99.91% | 99.32% | 99.90% |
| Upside Downs | 99.95% | 100.00% | 100.00% |

*LM = Late Middle Dead (death occurred between Day 15 and Day 18 of incubation)

Accuracy is defined as:

$$\text{Accuracy} = \left(1 - \frac{\text{\# of misidentified Eggs}}{\text{\# of total Eggs}}\right) * 100$$

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. An apparatus for candling eggs, comprising:
a carrier capable of supporting a plurality of eggs;
a thermal imaging camera;
one or more mirrors configured such that the camera, via the mirrors, is able to obtain a thermal image of both ends of the egg, either at the same time or sequentially; and
a processor in communication with the thermal imaging camera that is configured to analyze a thermal image of the eggs and obtain surface temperature information for each egg, wherein the processor is configured to designate an egg as non-live if the surface temperature of a central region of the downwardly facing surface of an egg compared to the surface temperature of a central region of the downwardly facing surface of adjacent eggs is lower by a predetermined amount.

2. The apparatus of claim 1, further comprising a plurality of parallel rollers that are configured to rotate the eggs as a thermal image is being obtained.

3. A method of candling eggs, comprising:
exposing a plurality of incubated eggs supported within a carrier to an environment having a temperature different from a temperature at which the eggs were incubated;
obtaining a thermal image of the eggs;
analyzing the thermal image to determine inverted eggs within the carrier,
wherein obtaining a thermal image of the eggs comprises obtaining a thermal image of downwardly facing surfaces of the eggs in the carrier, and further comprising designating an egg as an inverted egg if the downwardly facing surface has two regions with respective different temperatures, and wherein the temperature difference is greater than a predetermined amount.

4. The method of claim 3, wherein the two regions each comprise at least 10% of the total surface area of the egg in the thermal image.

5. The method of claim 3, wherein the two regions include a central region and a peripheral region that circumscribes the central region, and wherein the surface temperature of the central region is lower than the surface temperature of the peripheral region.

6. The method of claim 3, wherein obtaining a thermal image of the eggs comprises obtaining a thermal image of downwardly facing surfaces of the eggs in the carrier, and further comprising designating an egg as a not inverted egg if the temperature of the downwardly facing surface of the egg is uniform thereacross.

7. A method of candling eggs, comprising:
exposing a plurality of incubated eggs supported within a carrier to an environment having a temperature different from a temperature at which the eggs were incubated;
obtaining a thermal image of the eggs;
analyzing the thermal image to determine inverted eggs within the carrier,
wherein obtaining a thermal image of the eggs comprises obtaining a thermal image of upwardly facing surfaces of the eggs in the carrier, and further comprising designating an egg as an inverted egg if the temperature of the upwardly facing surface of the egg is uniform thereacross.

8. An apparatus for candling eggs, comprising:
a carrier capable of supporting a plurality of eggs;
a thermal imaging camera;
one or more mirrors configured such that the camera, via the mirrors, is able to obtain a thermal image of both ends of the egg, either at the same time or sequentially; and
a processor in communication with the thermal imaging camera that is configured to analyze a thermal image of the eggs to determine inverted eggs within the carrier.

9. The apparatus of claim 8, wherein the thermal imaging camera is configured to obtain a thermal image of upwardly facing surfaces of the eggs in the carrier, and wherein the processor is configured to designate an egg as an inverted egg if the surface temperature of the egg compared to the surface temperature of adjacent eggs is higher by a predetermined amount.

10. The apparatus of claim 8, wherein the processor is configured to calculate the difference between the surface temperature of each egg with the average surface temperature of adjacent eggs and to designate an egg as inverted if a surface temperature of the egg exceeds the average surface temperature of adjacent eggs by a predetermined amount.

11. The apparatus of claim 8, wherein the thermal imaging camera is configured to obtain a thermal image of upwardly and downwardly facing ends of the eggs, and wherein the processor is configured to compare the respective top and bottom thermal images to determine which surface of each egg has the higher temperature, and to designate an egg as inverted if the temperature of the upwardly facing surface is higher than the temperature of the respective downwardly facing surface.

12. An apparatus for candling eggs, comprising:
a thermal imaging camera configured to obtain a thermal image of a plurality of eggs supported within a carrier; and
a processor in communication with the thermal imaging camera that is configured to analyze a thermal image of the eggs to determine inverted eggs within the carrier,
wherein the thermal imaging camera is configured to obtain a thermal image of downwardly facing surfaces of the eggs in the carrier, and wherein the processor is configured to designate an egg as an inverted egg if the downwardly facing surface has two regions with respective different temperatures, and if the temperature difference is greater than a predetermined amount.

13. The apparatus of claim 12, wherein the thermal imaging camera is configured to obtain a thermal image of downwardly facing surfaces of the eggs in the carrier, and wherein the processor is configured to designate an egg as a not inverted egg if the temperature of the downwardly facing surface of the egg is uniform thereacross.

14. An apparatus for candling eggs, comprising:
a thermal imaging camera configured to obtain a thermal image of a plurality of eggs supported within a carrier; and
a processor in communication with the thermal imaging camera that is configured to analyze a thermal image of the eggs to determine inverted eggs within the carrier,
wherein the thermal imaging camera is configured to obtain a thermal image of upwardly facing surfaces of the eggs in the carrier, and wherein the processor is configured to designate an egg as an inverted egg if the temperature of the upwardly facing surface of the egg is uniform thereacross.

15. A method of candling eggs, comprising:
exposing a plurality of incubated eggs supported within a carrier to an environment having a temperature different from a temperature at which the eggs were incubated;
obtaining a thermal image of the eggs; and
analyzing the thermal image to determine eggs having an air cell located on a side portion thereof,
wherein obtaining a thermal image of the eggs comprises obtaining a thermal image of downwardly facing surfaces of the eggs in the carrier, and further comprising designating an egg as having an air cell located on a side portion of the egg if the temperature of a side portion of the egg surface is lower than a temperature of the remaining portion of the egg surface.

16. A method of candling eggs, comprising:
exposing a plurality of incubated eggs supported within a carrier to an environment having a temperature different from a temperature at which the eggs were incubated;
obtaining a thermal image of the eggs; and
analyzing the thermal image to determine eggs having an air cell located on a side portion thereof,
wherein obtaining a thermal image of the eggs comprises obtaining a thermal image of upwardly facing surfaces of the eggs in the carrier, and further comprising designating an egg as having an air cell located on a side portion of the egg if the temperature of a side portion of the egg surface is lower than a temperature of the remaining portion of the egg surface.

17. An apparatus for candling eggs, comprising:
a plurality of eggs supported in a carrier;
a thermal imaging camera;
one or more mirrors configured such that the camera, via the mirrors, is able to obtain a thermal image of both ends of the egg, either at the same time or sequentially; and
processor in communication with the thermal imaging camera that is configured to analyze a thermal image of the eggs and obtain surface temperature information for each egg.

18. An apparatus for candling eggs, comprising:
a thermal imaging camera configured to obtain a thermal image of a plurality of eggs supported in a carrier; and
processor in communication with the thermal imaging camera that is configured to analyze a thermal image of the eggs and obtain surface temperature information for each egg,
wherein the thermal imaging camera is configured to obtain a thermal image of downwardly facing surfaces of the eggs in the carrier, and wherein the processor is configured to designate an egg as having an air cell located on a side portion of the egg if the temperature of a side portion of the egg surface is lower than a temperature of the remaining portion of the egg surface.

19. An apparatus for candling eggs, comprising:
a thermal imaging camera configured to obtain a thermal image of a plurality of eggs supported in a carrier; and
processor in communication with the thermal imaging camera that is configured to analyze a thermal image of the eggs and obtain surface temperature information for each egg,
wherein the thermal imaging camera is configured to obtain a thermal image of upwardly facing surfaces of the eggs in the carrier, and wherein the processor is configured to designate an egg as having an air cell located on a side portion of the egg if the temperature of a side portion of the egg surface is lower than a temperature of the remaining portion of the egg surface.

20. The apparatus of claims 12, 14, 18, 19 or 13, wherein the thermal imaging camera is utilized with one or more mirrors configured such that the camera, via the mirrors, is able to obtain a thermal image of both ends of the egg, either at the same time or sequentially.

* * * * *